United States Patent [19]

Keppel et al.

[11] Patent Number: 4,670,415

[45] Date of Patent: Jun. 2, 1987

[54] PROCESS FOR THE PREPARATION OF IRON/LITHIUM -PROMOTED CATALYSTS FOR THE PRODUCTION OF MALEIC ANHYDRIDE

[75] Inventors: Robert A. Keppel, Chesterfield; Victoria M. Franchetti, St. Charles, both of Mo.

[73] Assignee: Monsanto Company, St. Louis, Mo.

[21] Appl. No.: 791,977

[22] Filed: Oct. 28, 1985

[51] Int. Cl.$^4$ .................. B01J 27/198; B01J 27/185; C07D 307/34
[52] U.S. Cl. ................................. 502/209; 502/213; 549/260; 549/259
[58] Field of Search ................ 502/209, 213

[56] References Cited

U.S. PATENT DOCUMENTS

| | | | |
|---|---|---|---|
| 3,296,282 | 1/1967 | Kerr | 549/260 X |
| 3,888,886 | 6/1975 | Young et al. | 502/209 X |
| 3,980,585 | 9/1976 | Ken et al. | 502/209 |
| 4,017,521 | 4/1977 | Schneider | 549/259 |
| 4,018,709 | 4/1977 | Barone et al. | 502/209 X |
| 4,111,963 | 9/1978 | Mount et al. | 502/209 X |
| 4,251,390 | 2/1981 | Barone | 502/209 |
| 4,276,222 | 6/1981 | Mount et al. | 502/209 X |
| 4,283,288 | 8/1981 | Udovich et al. | 502/209 |
| 4,293,498 | 10/1981 | Lenenski et al. | 549/260 X |
| 4,312,787 | 1/1982 | Dolhyj et al. | 502/209 |
| 4,317,778 | 3/1982 | Blum et al. | 502/209 X |
| 4,351,773 | 9/1982 | Milbeyer et al. | 502/209 X |
| 4,382,876 | 5/1983 | Neubold et al. | 502/209 |
| 4,435,521 | 3/1984 | Young et al. | 502/209 |
| 4,447,638 | 5/1984 | Goffney et al. | 502/209 X |
| 4,448,893 | 5/1984 | Bremer et al. | 502/209 |
| 4,515,899 | 5/1985 | Click et al. | 549/260 X |
| 4,515,904 | 5/1985 | Edwards | 502/209 |
| 4,518,523 | 5/1985 | Blum et al. | 502/209 |
| 4,525,471 | 6/1985 | Bremer et al. | 502/213 X |

Primary Examiner—Andrew H. Metz
Assistant Examiner—William G. Wright
Attorney, Agent, or Firm—Wendell W. Brooks; A. E. Hoffman; Arnold H. Cole

[57] ABSTRACT

Iron/lithium promoted phosphorus-vanadium-oxygen catalysts for the production of maleic anhydride are prepared by contacting a substantially tetravalent vanadium-containing compound and a phosphorus-containing compound and a promoter component containing each of iron and lithium in a substantially anhydrous alcohol medium in the presence of anhydrous hydrogen chloride to form an iron/lithium promoted phosphorus-vanadium-oxygen catalyst precursor. The catalyst precursor is recovered, dried, roasted, formed into structures if structures are desired, and calcined.

15 Claims, No Drawings

PROCESS FOR THE PREPARATION OF IRON/LITHIUM-PROMOTED CATALYSTS FOR THE PRODUCTION OF MALEIC ANHYDRIDE

FIELD OF THE INVENTION

This invention relates to a process for the preparation of phosphorus-vanadium-oxygen oxidation catalysts. More particularly, this invention relates to a process for the preparation of iron/lithium-promoted phosphorus-vanadium-oxygen catalysts. Such catalysts are useful for the partial oxidation of non-aromatic hydrocarbons in the vapor phase with molecular oxygen or a molecular oxygen-containing gas to produce maleic anhydride in excellent yields.

Maleic anhydride is of significant commercial interest throughout the world. It is used alone or in combination with other acids in the manufacture of alkyd and polyester resins. It is also a versatile intermediate for chemical synthesis. Significant quantities of maleic anhydride are produced each year to satisfy these varied needs.

DESCRIPTION OF THE PRIOR ART

Numerous catalysts containing phosphorus, vanadium, and oxygen (sometimes referred to as mixed oxides of phosphorus and vanadium) are disclosed in the prior art as being useful for the conversion of various organic feedstocks to maleic anhydride, and further that such catalysts wherein the valence of the vanadium is below +5, usually between about +3.8 and +4.8, are particularly well suited for the production of maleic anhydride from saturated hydrocarbons having at least four carbon atoms in a straight chain. In many instances, these catalysts also contain added promoter elements or components which are considered to exist in the catalyst as oxides. Common organic feedstocks include nonaromatic hydrocarbons such as n-butane, 1- and 2-butenes, 1,3-butadiene, or mixtures thereof.

Procedures for the preparation of catalysts containing the mixed oxides of phosphorus and vanadium and promoter components are also disclosed and taught by the prior art. Many of such procedures teach that it is preferable to reduce the vanadium in solution to the tetravalent state. For example, these catalysts can be prepared by contacting phosphorus-containing compounds, vanadium-containing compounds, and promoter component-containing compounds under conditions sufficient to produce the tetravalent vanadium and to form the promoter component-containing catalysts precursor. The catalyst precursor is thereafter recovered, dried, and calcined to produce the active catalyst.

U.S. Pat. No. 4,312,787 describes catalysts which comprise an inert support and a catalytically active mixed oxide material coating on the outer surface of the support in an amount greater than 50% to about 80% by weight of the combined support and oxide material. Such coating may be composed of oxides of phosphorus and vanadium or, alternatively, of oxides of phosphorus, vanadium, and uranium. Catalysts within the scope of the claims of the patent are reported to produce maleic anhydride from n-butane in yields ranging from 53% to 62.5%, with selectivities ranging from 57.4% to 67.9%.

In U.S. Pat. No. 4,251,390, a zinc-promoted phosphorus-vanadium-oxygen catalyst is disclosed and claimed. The catalyst is prepared by reducing pentavalent vanadium in a substantially anhydrous organic medium to a lower valence state and digesting the reduced vanadium in the presence of a zinc promoter compound. The resulting catalyst is activated by bringing the catalyst to operating temperatures for the oxidation of n-butane to maleic anhydride at a rate of 5° C. to 10° C. per hour in the presence of a butane-in-air mixture.

U.S. Pat. No. 4,018,709 discloses a process for the vapor phase oxidation of C₄ n-hydrocarbons using catalysts containing vanadium, phosphorus, uranium, or tungsten or a mixture of elements from zinc, chromium, uranium, tungsten, cadmium, nickel, boron, and silicon. In a preferred embodiment, the catalyst also contains an alkali metal or an alkaline earth metal, especially lithium, sodium, magnesium, or barium as active components. Typically, such catalysts are prepared in concentrated (37%) hydrochloric acid.

U.S. Pat. No. 4,002,650 discloses a process for the oxidation of n-butane using a catalyst of the formula

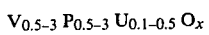

$$V_{0.5-3} P_{0.5-3} U_{0.1-0.5} O_x$$

wherein x is a number taken to satisfy the valence requirements of the other elements present. In a preferred preparative procedure, a mixture of vanadium pentoxide, concentrated hydrochloric acid, and uranyl acetate is heated under reflux. To this refluxing mixture is added 85% phosphoric acid. The resulting mixture is evaporated at atmospheric pressure and dried at 110° C., ground and screened to a suitable particle size, and activated by heating in an air flow at 482° C. for sixteen hours.

In U.S. Pat. No. 3,980,585, a process is disclosed for the preparation of maleic anhydride from normal C₄ hydrocarbons in the presence of a catalyst containing vanadium, phosphorus, copper, oxygen, tellurium or a mixture of tellurium and hafnium or uranium or a catalyst containing vanadium, phosphorus, copper, and at least one element selected from the group of tellurium, zirconium, nickel, cerium, tungsten, palladium, silver, manganese, chromium, zinc, molybdenum, rhenium, samarium, lanthanum, hafnium, tantalum, thorium, cobalt, uranium, and tin, optionally (and preferably) with an element from Groups 1a (alkali metals) or 2a (alkaline earth metals).

U.S. Pat. No. 3,888,866 discloses a process for the oxidation of n-butane by contacting the n-butane at a temperature from about 300° C. to about 600° C. with a phosphorus-vanadium-oxygen catalyst having a phosphorus/vanadium atom ratio of 0.5-2, promoted or modified with chromium, iron, hafnium, zirconium, lanthanum, and cerium, the promoter metal/vanadium atom ratio between about 0.0025 and about 1. The catalysts are prepared by refluxing a reaction mixture of vanadium oxide, phosphoric acid, a hydrogen halide (usually hydrochloric acid), and a specified promoter metal-containing compound. The resulting catalyst precursors are recovered, dried, formed into structures, and calcined to produce the active catalysts.

U.S. Pat. No. 3,862,146 discloses a process for the oxidation of n-butane to maleic anhydride in the presence of a phosphorus-vanadium-oxygen catalyst complex, promoted or activated with a zinc, bismuth, copper, or lithium activator. The phosphorus/vanadium and activator/vanadium atom ratios are from about 0.5-5 and from about 0.05-0.5, respectively.

U.S. Pat. No. 3,856,824 discloses a process for the production of maleic anhydride by oxidation of saturated aliphatic hydrocarbons in the presence of a catalyst comprising phosphorus, vanadium, iron, oxygen and an added modifier comprising chromium combined with at least one element selected from the group consisting of nickel, boron, silver, cadmium, and barium.

European Patent Application No. 98,039 discloses a process for the preparation of phosphorus-vanadium mixed oxide catalyst, optionally containing an added promoter element selected from the group consisting of Group 1a (alkali metals), Group 2a (alkaline earth metals), titanium, chromium, tungsten, niobium, tantalum, manganese, thorium, uranium, cobalt, molybdenum, iron, zinc, hafnium, zirconium, nickel, copper, arsenic, antimony, tellurium, bismuth, tin, germanium, cadmium, and lanthanides, and mixtures thereof. The catalyst, which exhibit a phosphorus/vanadium atom ratio from 0.8 to 1.3 and a promoter/vanadium atom ratio from 0.01 to 0.5, are prepared in an organic liquid reaction medium capable of reducing the vanadium to a valence state of approximately +4 to form a non-solubilized catalyst precursor, contacting the non-solubilized catalyst precursor containing organic liquid with water to form a two-phase system having an upper organic liquid phase and a lower non-solubilized catalyst precursor-containing aqueous phase, drying the catalyst precursor, and calcining. The catalysts so obtained reportedly are useful in the production of maleic anhydride from normal $C_4$ hydrocarbons.

Although these prior art processes generally are effective to provide the desired catalyst, the commercial utility of a catalyst system and a catalytic process is highly dependent upon the cost of the catalyst employed, the conversion of the reactant(s), and the yield of the desired product. In many instances, a reduction in the cost of a catalyst system on the order of a few cents per kilogram or pound, a small percent increase in the yield of the desired product, relative to the amount of catalyst required, represents a tremendous commercial economical saving and advantage. Accordingly, research efforts are continually being made to define new or improved catalyst systems and methods and processes of making new and old catalyst systems to reduce the cost and/or upgrade the activity and selectivity of such catalyst systems in such processes. The discovery of the process of the instant invention, therefore, is believed to be a decided advance in the catalyst art.

SUMMARY OF THE INVENTION

It is an object of this invention to provide a process for the preparation of improved catalysts comprising phosphorus, vanadium, and oxygen and a promoter component containing each of iron and lithium useful for the oxidation of nonaromatic hydrocarbons to produce maleic anhydride.

Another object of this invention is to provide a process for the preparation of improved catalysts comprising phosphorous, vanadium, and oxygen and a promoter component containing each of iron or lithium useful for the production of maleic anhydride in excellent yields.

To achieve these and other objects, together with the advantages thereof, which will become apparent from the accompanying description and claims, a process is provided which comprises:

(a) contacting at least one of each of a substantially tetravalent vanadium-containing compound and a phosphorus-containing compound and a promoter component containing each of iron and lithium in a substantially anhydrous alcohol medium in the presence of anhydrous hydrogen chloride to form a catalyst precursor;

(b) recovering the catalyst precursor;
(c) drying the catalyst precursor;
(d) roasting the catalyst precursor; and
(e) calcining the roasted catalyst precursor to form the active catalyst.

DESCRIPTION OF THE PREFERRED EMBODIMENTS

In accordance with this invention, a process is provided for the preparation of catalysts which are useful for the partial oxidation of nonaromatic hydrocarbons having at least four carbon atoms in a straight chain with molecular oxygen or a molecular oxygen-containing gas in the vapor phase to maleic anhydride. These catalysts, which comprise phosphorus, vanadium, and oxygen and a promoter component containing each of iron and lithium, exhibit excellent selectivities to, and yields of, maleic anhydride.

The catalysts prepared in accordance with the process of the instant invention have a phosphorus-to-vanadium (phosphorus/vanadium or P/V) atom ratio from about 0.50 to about 2.00, with a P/V atom ratio of about 0.95 to about 1.20 being preferred. The total atom ratio of iron and lithium to vanadium [(iron+lithium)/vanadium or (Fe+Li)/V] advantageously is in the range from about 0.0025 to about 0.0080, with the proviso that the Fe/V atom ratio is in the range from about 0.0010 to about 0.0040, preferably about 0.0015 to about 0.0035, and the Li/V atom ratio is from about 0.0015 to about 0.0040, preferably from about 0.0025 to about 0.0035, most preferably about 0.0030, and with the further proviso that the Fe/Li atom ratio is from about 0.30 to about 1.30.

For purposes of this invention, the term "yield" means the ratio of the moles of maleic anhydride obtained to the moles of hydrocarbon feedstock introduced into the reactor multiplied by 100, the term expressed as mole percent. The term "selectivity" means the ratio of moles of maleic anhydride obtained to the moles of hydrocarbon feedstock reacted or converted multiplied by 100, the term expressed as mole percent. The term "conversion" means the ratio of the moles of hydrocarbon feedstock reacted to the moles of hydrocarbon introduced into the reactor multiplied by 100, the term expressed as mole percent. The term "space velocity" or "gas hourly space velocity" or "GHSV" means the hourly volume of gaseous feed expressed in cubic centimeters (cc) at 20° C. and atmospheric pressure, divided by the catalyst bulk volume, expressed in cubic centimeters, the term expressed as cc/cc/hour or $hr^{-1}$.

Component source materials suitable for use in the process of the instant invention are those which yield the unique catalysts prepared in accordance with the process of the instant invention. Representatives vanadium-containing compounds useful as a source of vanadium in the catalysts of the instant invention are vanadium oxides, such as vanadium tetroxide and vanadium pentoxide; vanadium oxyhalides, such as vanadyl dichloride, vanadyl trichloride, vanadyl dibromide, and vanadyl tribromide; vanadium-containing acids, such as metavanadic acid and pyrovanadic acid; and vanadium salts, both organic and inorganic, such as ammonium metavanadate, vanadium oxysulfate (vanadyl sulfate), vanadyl formate, vanadyl acetoacetonate, vanadyl oxalate, vanadyl alkoxides, and mixtures thereof. Among these compounds, vanadium pentoxide is preferred.

The phosphorus-containing compounds useful as a source of phosphorus in the catalysts prepared in accordance with the process of the instant invention are those well known to the art. Suitable phosphorous-containing compounds include phosphoric acid, such as metaphosphoric acid, orthophosphoric acid, triphosphoric acid, and pyrophosphoric acid; phosphorus oxides, such as phosphorus pentoxide; phosphorus halides and oxyhalides, such as phosphorus oxyiodide, phosphorus pentachloride, and phosphorus oxybromide; phosphorus salts, such as mono-, di-, and triammonium phosphates; and organophosphorus compounds, such as ethyl phosphate and methyl phosphate and mixtures thereof. Of these phosphorus-containing compounds, the phosphoric acids, such as orthophosphoric acid and pyrophosphoric acid and mixtures thereof are preferred. More specifically, phosphoric acid is employed as substantially anhydrous phosphoric acid, for example, orthophosphoric acid. Polyphosphoric acid is another preferred type of anhydrous phosphoric acid. This latter acid is commercially available as a mixture of orthophosphoric acid with pyrophosphoric (diphosphoric), triphosphoric, and higher acids, and is sold on the basis of its calculated content of $H_3PO_4$, as, for example 115%. Superphosphoric acid is a similar mixture sold at 105% $H_3PO_4$. Such acids (having calculated $H_3PO_4$ concentrations greater than 100% revert primarily to orthophosphoric acid upon dilution with water.

In addition to phosphorus, vanadium, and oxygen, the catalysts of the instant invention, as previously noted, also comprise a promoter component containing each of iron and lithium. Such promoter components are readily introduced into the catalysts during the formation of the catalyst precursor (as discussed herein below) by adding the promoter component to the reaction solution as separate compounds together with the vanadium-containing compound or separately introducing such compounds into the reaction solution. The promoter component-containing compounds, however, should be at least partially soluble in the reaction medium (alcohol medium and the added anhydrous hydrogen chloride).

As a source of iron for the iron promoter component, various iron-containing compounds, both ferric and ferrous, may be employed. Suitable iron-containing compounds include iron halides, phosphates, oxides, carbonates, sulfates, nitrates, acetates, oxalates, citrates, and the like. Metallic iron also may be employed, and, in general, is the iron source material of choice.

The lithium-containing compounds useful as a source material for the lithium promoter component are not narrowly critical. Suitable lithium-containing compounds include lithium halides, phosphate, oxide, hydroxide, carbonate, sulfate, nitrate, acetate, oxalate, citrate, and the like. Among these compounds, lithium chloride (a lithium halide) is generally preferred.

The process of the instant invention, broadly described, involves contacting at least one of each of a vanadium-containing compound, a phosphorus-containing compound, and a promoter component as at least one of each of an iron-containing compound (including metallic iron) and a lithium-containing compound in an alcohol medium (as described hereinbelow) in a manner and under conditions capable of reducing the vanadium (if required) to a desired valence state (less than +5) in the presence of anhydrous hydrogen chloride in an amount sufficient to dissolve the vanadium-containing compound in the alcohol medium and to react the phosphorus-containing compound with the reduced vanadium-containing compound and the promoter component to form catalyst precursors, recovering the catalyst precursors, forming the catalyst precursors into structures (if structures are desired), and calcining the catalyst precursors to form the catalysts.

The contacting of the vanadium-containing compound, the phosphorus-containing compound and the promoter component may be accomplished in any convenient manner. In one embodiment, the phosphorus-containing compound may be introduced into a suspension (solution) of the vanadium-containing compound/promoter component/alcohol medium mixture, either prior to or subsequent to the addition of the anhydrous hydrogen chloride gas, in the form of a solution or suspension in the alcohol medium, or, when the phosphorus-containing compound is in liquid form, such as 100% phosphoric acid, it may be added alone. Alternatively, the vanadium-containing compound, the phosphorus-containing compound, and the promoter component can be introduced simultaneously into the alcohol medium, followed by contacting the mixture with the anhydrous hydrogen chloride gas. In yet another mode, the vanadium-containing compound and the promoter component are introduced into a solution or dispersion of the phosphorus-containing compound in the alcohol medium. In a preferred embodiment, however, the vanadium-containing compound and the promoter component are introduced into a solution of the phosphorus-containing compound in the alcohol medium and the mixture contacted with anhydrous hydrogen chloride gas.

The alcohols suitable for use as the alcohol medium in the instant process must be capable of functioning as a solvent and/or suspending agent for the vanadium-containing compound and the promoter component-containing compounds, as a solvent and/or diluent for the phosphorus-containing compound, and where needed, a mild reducing agent for the vanadium-containing compound and preferably, as a suspending agent for the catalyst precursors. Thus, it is preferred that the alcohol is not a solvent for the catalyst precursors. In those instances wherein the catalyst precursor is soluble in the alcohol medium, however, precipitation should be readily induced by removal of a portion of the alcohol. Suitable alcohols include primary and secondary alcohols, such as methanol, ethanol, 1-propanol, 2-propanol, 2-methyl-1-propanol (isobutyl alcohol), 3-methyl-2-butanol, 2,2-dimethyl-1-propanol, 1,2-ethanediol (ethylene glycol). Of these alcohols, isobutyl alcohol is preferred because of its ready availability, its relatively low cost, and its convenient boiling point (108° C.).

When a pentavalent vanadium-containing compound, such as the preferred vanadium pentoxide, $V_2O_5$, is employed as the vanadium source material, it must be reduced (at least in part) to the tetravalent state. The desired reduction is readily accomplished by contacting the pentavalent vanadium with the alcohol medium (and the anhydrous hydrogen chloride) either in the presence or absence of the phosphorus-containing compound and the promoter component, and the resulting mixture heated to a temperature sufficient to achieve the appropriate average vanadium valence state. As is well known to those skilled in the art, anhydrous hydrogen chloride can serve to dissolve vanadium-containing compounds in an alcohol medium and thereby enhance the rate of pentavalent vanadium reduction. Preferably, the pentavalent vanadium, as previously noted, is only partially reduced by heating it in the alcohol medium until the desired valence state of less than +5 is achieved, most preferably an average valence state between about +3.9 to about +4.6 or simply about 3.9 to about 4.6. In general, suitable reduction is indicated to have been achieved when the color of the reaction mixture (solution) turns blue, such color being indicative of a vanadium valence of between about 3.9 to about 4.6.

The vanadium reduction temperature will depend on the reducing strength of the alcohol medium selected and can vary widely. Accordingly, while any temperature effective to reduce the vanadium-containing compound is suitable, such effective temperatures typically will vary from about 30° C. to about 300° C., preferably from about 60° C. to about 200° C., preferably from about 80° C. to about 150° C. Preferably, the alcohol medium selected will boil at about the selected temperature so the reaction can be conducted by refluxing. Thus, when isobutyl alcohol is used as the alcohol medium, simple refluxing at about 108° C. [$1.013 \times 10^2$ kPa-G (1 atm)] for a period of from about five hours to about eight hours will suffice. The reaction mixture preferably is maintained in the substantially anhydrous state by removing any water formed in situ by azeotropic distillation or other suitable means. By "substantially anhydrous" as used herein is meant typically less than about 10%, preferably less than about 5%, and most preferably less than about 1%, by weight water, based on the weight of the alcohol medium in the reaction mixture. As previously noted, anhydrous hydrogen chloride serves to dissolve the vanadium-containing compound to create a homogeneous solution of the vanadium containing compound in the alcohol medium and thereby enhance the rate of reduction of the pentavalent vanadium.

The alcohol medium is employed in amounts effective to achieve the appropriate vanadium reduction, where needed, to provide uniform heating of the vanadium-containing compound, and preferably to provide a solution which can be conveniently refluxed at the selected reduction temperature. Thus, while any effective amount of alcohol can be employed, such effective amounts typically will constitute from about 50% to about 90% by weight, based on the combined weight of the alcohol medium the vanadium-containing compound and, if present, the promoter component.

When the reduction of the vanadium-containing compound to a valence state of less than +5 is carried out in the absence of either or both of the phosphorus-containing compound and/or the promoter component, the entire solution of alcohol medium and the reduced vanadium-containing compound is cooled to a temperature between about 20° C. and about 50° C., and combined with a solution of the phosphorus-containing compound dissolved in a similar, preferably the same, alcohol medium and, if necessary, the promoter component to form a reaction mixture. The reaction mixture is then heated, preferably refluxed, to reduce and/or react the vanadium-containing compound with the phosphorus-containing compound (and the promoter component) at temperatures of typically from about 30° C. to about 300° C., preferably from about 60° C. to about 200° C., preferably from about 80° C. to about 150° C., for a period of typically from about one hour to about 50 hours, preferably from about 10 hours to about 35 hours, and most preferably from about 15 hours to about 25 hours to form the catalyst precursor. The above reaction, as previously noted for the vanadium-reduction reaction, preferably is conducted to maintain the reaction mixture in the substantially anhydrous state, preferably by azeotropic distillation to remove any water formed in situ.

In those instances where the vanadium-containing compound already possesses an average vanadium valence of between about 3.9 and about 4.6, the separate vanadium-reduction step can be eliminated and the vanadium-containing compound reacted directly with the phosphorus-containing compound (and the promoter component) in the alcohol medium as previously described.

The reaction pressure for the catalyst precursor-forming reaction is not critical and can be subatmospheric, atmospheric, or superatmospheric, provided the reactants and alcohol medium do not volatilize to such an extent that the composition of the reaction mixture is altered substantially from the description provided herein. Atmospheric pressure is preferred.

Advantageously, the catalyst precursor-forming reaction is conducted under sufficient agitation to assure uniform reacting, and interaction between the reactants, during reaction. This can be achieved by conventional high speed agitation equipment capable of achieving a high degree of mixing.

Upon completion of the reaction, it is necessary to recover the resulting catalyst precursor from the substantially homogeneous reaction mixture. In general, this may be achieved by removing a portion of the alcohol medium to induce precipitation of the catalyst precursor. The reaction mixture may then be cooled to between 20° C. and 50° C. and the catalyst precursor separated from the alcohol medium. This separation can be accomplished by a variety of conventional techniques well known to those skilled in the art, including filtration, centrifugation and decantation of the supernatent liquid alcohol medium from the solid catalyst precursor, and evaporating the alcohol medium to form a cake or paste of the catalyst precursor.

The recovered catalyst precursor is then typically subjected to conditions sufficient to remove most of the remaining alcohol. This can be achieved by drying, preferably continuous drying, to evaporate such alcohol. Before final drying is conducted, if desired, the recovered catalyst precursor can be washed in the alcohol (of the alcohol medium) one or more times to remove any residual unreacted phosphorus-containing compound and/or any other alcohol-soluble species occluded in the catalyst precursor, followed by a repetition of the catalyst precursor recovery procedures previously described.

Drying can be achieved by exposing the catalyst precursor to air at room temperature for a period of from about one hour to about 100 hours or by placing it in a forced hot air oven maintained at a temperature of less than about 180° C., typically between about 100° C. and about 150° C. for about one hour to about 10 hours. Alternatively, the catalyst precursor can be air dried at room temperature for between about one hour and about 48 hours and then placed in the forced hot air oven. Drying of the catalyst precursor preferably should be conducted at temperatures below those at which crystal phase transitions occur and until a level of nearly constant weight is achieved. Drying under reduced pressure at room or elevated temperature, as previously described, also can be employed as a suitable alternative.

After the catalyst precursor has been recovered and dried, it is then formed into structures, if structures are desired, suitable for use in a maleic anhydride reactor, although nonstructured, powder can be employed. Techniques for forming appropriate structures from the catalyst precursors for use in a fixed bed, heat exchanger type reactor or in a fluidized bed reactor are well known to those skilled in the art. For example, the catalyst precursors can be structured in unsupported form for use in a fixed bed, heat exchanger type reactor by prilling or tableting, extruding, sizing, and the like. Suitable binding and/or lubricating agents for pelleting or tableting include Sterotex ®, starch, calcium stearates, stearic acid, and graphite. Extrusion of the catalyst precursor can be achieved by forming a wet paste which does not slump and extruding the paste. Similarly, the catalyst precursors can be comminuted for use in a fluidized bed reactor.

The catalyst precursors also can be supported on support materials or carriers for use in either fixed or fluidized bed operations. Nonlimiting representative carriers include alumina, silica, silica-gel, silicon carbide, ceramic donuts, magnesia, titania, and titania-silica.

In a preferred embodiment, the catalyst precursor, whether structured, nonstructured, supported, nonsupported, or any combination thereof, is roasted at a temperature from about 200° C. to about 290° C., preferably from about 250° C. to about 275° C., for a suitable period of time, usually at least two hours, preferably from about four hours to about eight hours, to remove residual traces of organic materials. In a most preferred embodiment, the catalyst precursors are roasted by heating in a nitrogen-purged furnace to about 260° C. over a one-hour period, maintaining this temperature over an additional six-hour period, and purging the roasting furnace with dry air at the (beginning of the) fourth hour of the temperature maintenance or hold period, the embodiment conveniently designated as 1(260)6 roasting.

The catalyst precursors, prior to use, must be calcined/activated (hereinafter conveniently referred to as calcined or cognate words, such as calcine and calcination) in order to convert the catalyst precursor into the active catalyst. This may be accomplished by heating the catalyst precursor in a selected atmosphere at a selected elevated temperature either in a separate step or, preferably, in situ in the reactor in which the catalyst will be used for the production of maleic anhydride. During such calcination, it is desirable, although not essential, to maintain a steady flow of the calcination atmosphere over the catalyst precursor surface. Suitable space velocities for the atmosphere typically range from about 50 hr$^{-1}$ to about 150 hr$^{-1}$, usually about 100 hr$^{-1}$.

In a preferred embodiment, the catalyst precursor is charged to the maleic anhydride reactor and heated in a dry air atmosphere flowing at the previously noted space velocity to a temperature from about 100° C. to about 290° C., preferably from about 250° C. to about 290° C., for a suitable period of time, usually about two hours. Water is then optionally added to the flowing dry air stream in an amount sufficient to provide a water concentration up to about 10% by volume. Normally, a water concentration of about 1.5 volume percent to about two volume percent is sufficient. Thereafter, the temperature is increased to a value from about 300° C. to about 400° C., usually from about 350° C. to about 400° C., at a maximum rate of about 10° C. per hour, normally from about 1° C. to about 3° C. per hour, and any gaseous hydrocarbon described hereinafter as suitable for partial oxidation to maleic anhydride, preferably n-butane, is added to the flowing air stream in contact with the catalyst in an amount sufficient to provide a hydrocarbon concentration from about 0.5 mole percent to about 1.5 mole percent, preferably about 0.6 mole percent. The hydrocarbon is introduced at a temperature less than the phase transformation initiation temperature (normally from about 300° C. to about 315° C.). A hydrocarbon introduction temperature from about 275° C. to about 290° C. is preferred. The calcination temperature typically is maintained over a period ranging from about 0.5 hour to about 24 hours, preferably from about one hour to about six hours.

The catalysts prepared in accordance with the instant process, as previously noted, exhibit a P/V atom ratio from about 0.50 to about 2.00, with a P/V atom ratio of about 0.95 to about 1.20 being preferred. The catalysts also exhibit a total (Fe+Li)/V atom ratio from about 0.0025 to about 0.0080, with the proviso that the Fe/V atom ratio is from about 0.0010 to about 0.0040, preferably from about 0.0015 to about 0.0035 and the Li/V atom ratio is from about 0.0015 to about 0.0040, preferably from about 0.0025 to about 0.0035, most preferably about 0.0030, and with the further proviso that the Fe/Li atom ratio is from about 0.30 to about 1.30.

The catalysts of the instant process can be used (in a suitable reactor) to convert nonaromatic hydrocarbons to maleic anhydride. A mixture of hydrocarbon and a molecular oxygen-containing gas (including molecular oxygen), such as air, can be contacted with the catalysts at temperatures between about 300° C. and 600° C. at concentrations of from about one mole percent to about 10 mole percent hydrocarbon at a gas hourly space velocity (GHSV), or simply space velocity, up to about 4000 hr$^{-1}$ to produce maleic anhydride. However, the initial yield of maleic anhydride may be low; and if this is the case, the catalyst, as will occur to those skilled in the art, can be "conditioned" by contacting the catalyst with low concentrations of hydrocarbon and maleic oxygen-containing gas at low space velocities for a period of time before production operations begin.

The reaction to convert nonaromatic hydrocarbons to maleic anhydride requires only contacting the hydrocarbons admixed with a molecular oxygen-containing gas (including molecular oxygen), such as air or molecular oxygen-enriched air, with the catalyst at elevated temperatures. In addition to the hydrocarbon and molecular oxygen, other gases, such as nitrogen or steam, may be present or added to the reactant feed stream. Typically, the hydrocarbon is admixed with the molecular oxygen-containing gas, preferably air, at a concentration of about one mole percent to about 10 mole percent hydrocarbon and contacted with the catalysts at a space velocity of about 100 hr$^{-1}$ to about 4000 hr$^{-1}$ at a temperature between about 300° C. and about 600° C., preferably from about 1000 hr$^{-1}$ to about 3000 hr$^{-1}$ and from about 325° C. to about 425° C., to provide an excellent yield of, and selectivity to, maleic anhydride.

The catalysts prepared according to the instant process are useful in a variety of reactors to convert nonaromatic hydrocarbon to maleic anhydride. The catalysts may be used in a fixed-bed reactor using any of the structures previously described, such as, for example, tablets or pellets, or in a fluid-bed reactor using catalysts preferably having a particle size of less than 300 microns (μm). Details of the operation of such reactors are well known to those skilled in the art.

The catalysts prepared in accordance with the instant process are particularly useful in fixed bed (tube), heat exchanger type reactors. The tubes of such reactors can vary in diameter from about 0.635 cm (0.25 in.) to about 3.81 cm (1.50 in.) and the length can vary from about 15.24 cm (6 in.) to about 304.80 cm (10 ft) or more. It is desirable to have the surfaces of the reactors at relatively constant temperatures, and some medium to conduct heat from the reactors is necessary to aid temperature control. Nonlimiting examples of such media include Woods metal, molten sulfur, mercury, molten lead, and eutectic salt baths. A metal block reactor whereby the metal surrounding the tube acts as a temperature regulating body also can be used. The reactor or reactors can be constructed of iron, stainless steel, carbon steel, nickel, glass, such as Vycor, and the like.

Pressure is not critical in the reaction to convert nonaromatic hydrocarbons to maleic anhydride. The reaction may be conducted at atmospheric, superatmospheric, or subatmospheric pressure. It generally will be preferred, however, for practical reasons, to conduct the reaction at or near atmospheric pressure. Typically, pressures from about $1.013 \times 10^2$ kilopascals-gauge (kPa-G, 14.7 psig, 1 atm) to about $1.38 \times 10^2$ kPa-G (20.0 psig) may be conveniently employed.

Maleic anhydride produced by using the catalysts of the instant invention can be recovered by any means well known to those skilled in the art. For example, maleic anhydride can be recovered by direct condensation or by absorption in suitable media with subsequent separation and purification of the anhydride.

A large number of nonaromatic hydrocarbons having from four to 10 carbon atoms can be converted to maleic anhydride using the catalysts of the instant invention. It is only necessary that the hydrocarbon contain not less than four carbon atoms in a straight chain. As an example, the saturated hydrocarbon n-butane is satisfactory, but isobutane (2-methylpropane) is not satisfactory for conversion to maleic anhydride although its presence is not harmful. In addition to n-butane, other suitable saturated hydrocarbons include the pentanes, the hexanes, the heptanes, the octanes, the nonanes, the decanes, and mixtures of any of these, with or without n-butane so long as a hydrocarbon chain having at least four carbon atoms in a straight chain is present in the saturated hydrocarbon molecule.

Unsaturated hydrocarbons are also suitable for conversion to maleic anhydride using the catalysts of the instant invention. Suitable unsaturated hydrocarbons include the butenes, (1-butene and 2-butene), 1,3 butadiene, the pentenes, the hexenes, the heptenes, the octenes, the nonenes, the decenes, and mixtures of any of these, with or without the butenes, again, so long as the requisite hydrocarbon chain having at least four carbon atoms in a straight chain is present in the molecule.

Cyclic compounds such as cyclopentane and cyclopentene are also satisfactory feed materials for conversion to maleic anhydride.

Of the aforementioned feedstocks, n-butane is the preferred saturated hydrocarbon and the butenes are the preferred unsaturated hydrocarbons, with n-butane being most preferred of all feedstocks.

It will be noted that the aforementioned feedstocks need not necessarily be pure substances, but can be technical grade hydrocarbons.

The principal product from the oxidation of the aforementioned suitable feed materials is maleic anhydride, although small amounts of citraconic anhydride (methylmaleic anhydride) may also be produced when the feedstock is a hydrocarbon containing more than four carbon atoms.

The following specific examples illustrating the best currently-known method of practicing this invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

EXAMPLE 1

(a) Orthophosphoric Acid, 100%

A 3-liter, 4-neck, round bottom flask, equipped with a thermometer and a stainless steel paddle stirrer, was charged with 901.8 g (7.87 moles) of 85.5% orthophosphoric (phosphoric) acid ($H_3PO_4$). Stirring was commenced and 343.4 g (2.42 moles) of phosphorus pentoxide ($P_2O_5$) was added to the phosphoric acid, causing an exothermic reaction and an increase in temperature as high as 150° C. as the $P_2O_5$ dissolved. The resultant solution was stirred for 20 minutes at the elevated temperatures and thereafter cooled to ambient temperatures (approximately 25° C.).

(b) Catalysts

A 12-liter, 4-neck, round bottom flask equipped with a thermometer, coarse-frit gas dispersion tube, a paddle stirrer, and a water-cooled Dean Stark trap fitted with a Friedrich's condenser was charged with 8.3 l of isobutyl alcohol. Stirring was commenced and the isobutyl alcohol was cooled to 10°–15° C. To the cooled isobutyl alcohol was added over a 12-minute period the 100% phosphoric acid [1245.6 g (12.71 moles)] from Part (a) above, causing a temperature rise of 10° C. The solution of phosphoric acid in isobutyl alcohol was cooled to 5°–10° C. To this cooled solution was added, with stirring, 963.0 g (5.29 moles) of vanadium pentoxide ($V_2O_5$), followed by 1.35 g (0.032 mole) of lithium chloride (LiCl), 0.96 g (0.017 mole or g-atom) of iron powder, and an additional 1.0 l of isobutyl alcohol, a portion of which was used to rinse residual 100% phosphoric acid from its preparation vessel and transfer funnel into the reaction flask. The charged P/V atom ratio was about 1.20, the Fe/V atom ratio was about 0.0016, the Li/V atom ratio was about 0.0030, and the Fe/Li atom ratio was about 0.53. Anhydrous hydrogen chloride [HCl (2037.0 g, 55.81 moles)] gas was added via the gas dispersion tube to the isobutyl alcohol/$H_3PO_4$/$V_2O_5$/LiCl/Fe mixture over a 4.67-hour period. During the HCl addition, the temperature was maintained between 40° C. and 50° C. via a cooling bath. Upon completion of the HCl addition, at which time the initial yellow slurry had changed to a dark red-brown solution, the cooling bath was removed and replaced by a 12-1 heating mantle. The solution was heated to reflux (initially 98° C.) over a 2.5-hour period, and maintained at reflux (approximately 102° C.) over an additional two-hour period. During the heat-up period and the reflux period, copious amounts of HCl were evolved and the solution changed transitorily from an initial red-brown to a green-brown to a navy blue color. Thereafter, 5.4 l of distillate was removed at atmospheric pressure over a 5.0-hour period, followed by an additional 1.38-hour period of reflux, followed by removal of an additional 1.5 l of distillate over a 2.36-hour period, thereby removing a total of 6.9 l of distillate over a 7.36-hour distillate removal period. The turbid mixture was poured into two 4.445 cm (1.75 in)×24.13 cm (9.5 in)×37.465 cm (14.75 in) Pyrex brand cake pans and placed in an oven maintained at 140°–150° C. for 5.5 hours to yield 2225.0 g of dry catalyst precursor. The dry catalyst precursor was ground and sieved to −14, +18 (14/18) mesh (U.S. Standard Sieve Size; 1.0–1.4 mm) particles, placed in Pyrex brand casserole dishes, and roasted by heating in a nitrogen/purged furnace to 260° C. over a one-hour period, which temperature was maintained for three hours, followed by a gradual replacement of the nitrogen by air and heating an additional three hours to yield 1980.0 g of black catalyst precursor powder. The dry precursor powder was mixed with one weight percent of powdered graphite (which serves as a tableting lubricant) and pressed into 0.48-cm (0.1875-in) tablets having a side crush strength of 22.25–44.50 newtons [N, 5.00–10.00 pounds (lbs)]. The catalyst precursor tablets were calcined in situ in the presence of an atmosphere flowing at 100 hr$^{-1}$ total space velocity throughout the calcination period to convert the catalyst precursor into the active catalyst. The tablets were charged to a 2.12-cm (0.834-in.) inside diameter×335.28-cm (11-ft) long tubular fixed bed reactor maintained at 200° C. and heated in a flowing dry air atmosphere to 250° C. over a 3.124-hour period. Thereafter, the temperature was allowed to drop slightly to 230° C., at which time water was added to the flowing dry air stream in an amount sufficient to provide a water concentration of 1.8% by volume. The temperature was increased to 280° C. at a rate of 3° C. per hour and n-butane was added to the flowing water-containing air stream in an amount sufficient to provide an n-butane-in-air concentration of 0.6 mole percent. The tempertature was increased to 400° C. at a rate of 1° C. per hour and there maintained for a period of six hours, with the last five hours being conducted under a flowing stream of nitrogen gas. The catalyst was then performance tested in the calcination reactor at 1150 hr$^{-1}$ space velocity and 1.9 mole percent n-butane-in-air. The parameters and results are tabulated in Table 1.

EXAMPLE 2

The apparatus and procedure described in Example 1 was repeated except that 9.5 g (0.035 mole) of ferric chloride hexahydrate was employed to provide a charged Fe/V atom ratio of about 0.0033 and an Fe/Li atom ratio of about 1.094. The resultant catalyst was performance tested as described in Example 1. The parameters and results are tabulated in Table 1.

EXAMPLE 3

A catalyst was prepared using the apparatus and in accordance with the procedure described in Example 1 except that 0.785 g (0.014 mole) of iron powder was employed to provide a charged Fe/V atom ratio of about 0.0013 and Fe/Li atom ratio of about 0.44. The catalyst was performance tested as described in Example 1 except that the space velocity was 2600 hr$^{-1}$ and the n-butane-in-air concentration was 2.0 mole percent. The parameters and results are tabulated in Table 1.

EXAMPLE 4 (Comparative)

The apparatus and procedure described in Example 1 was repeated except that iron was omitted. The resultant catalyst was performance tested as described in Example 1 at 1150 hr$^{-1}$ space velocity and 1.9 mole percent n-butane-in-air (4a) and at 2600 hr$^{-1}$ space velocity and 2.0 mole percent n-butane-in-air (4b). The parameters and results are tabulated in Table 1.

TABLE 1

| EXAM. | EMPIRICAL FORMULA[2] | FORM (SIZE), cm | SPACE VELOCITY hr$^{-1}$ | n-BUTANE mole % | TEMP. °C. BATH | TEMP. °C. REAC. | CONV. mole % | SEL. mole % | YIELD mole % |
|---|---|---|---|---|---|---|---|---|---|
| 1 | $P_{1.20}V_{1.00}Fe_{0.0016}Li_{0.0030}O_x$ | Tablets (0.48) | 1150 | 1.9 | 413 | 451 | 78.1 | 69.8 | 54.5 |
| 2 | $P_{1.20}V_{1.00}Fe_{0.0033}Li_{0.0030}O_x$ | " | 1150 | 1.9 | 416 | 467 | 78.9 | 67.3 | 53.1 |
| 3 | $P_{1.20}V_{1.00}Fe_{0.0013}Li_{0.0030}O_x$ | " | 2600 | 2.0 | 427 | 482 | 71.4 | 67.9 | 48.5 |
| 4a[3] | $P_{1.20}V_{1.00}Li_{0.0030}O_x$ | " | 1150 | 1.9 | 430 | 467 | 78.8 | 64.9 | 51.1 |
| 4b[3] | $P_{1.20}V_{1.00}Li_{0.0030}O_x$ | " | 2600 | 2.0 | 436 | 482 | 69.4 | 65.7 | 45.6 |

[1]The catalysts were performance tested in 2.12-cm (0.834-in) inside diameter × 335.28-cm (11-ft) long tubular fixed bed reactor.
[2]Subscript x is a number taken to satisfy the average valence requirements of the remaining elements present.
[3]Comparative example.

Comparison of the performance of the catalysts prepared in accordance with the process of the instant invention with that of the comparative catalyst clearly demonstrates the advantages of the instant catalysts. In each instance, when compared at the same space velocity, the catalysts prepared in accordance with the process of the instant invention (Examples 1 and 2 at 1150 hr$^{-1}$ space velocity and Example 3 at 2600$^{-1}$ space velocity) demonstrates higher values for the conversion of n-butane and selectivity to, and yield of, maleic anhydride than those demonstrated by the comparative catalyst (Example 4a at 1150 hr$^{-1}$ space velocity and Example 4b at 2600 hr$^{-1}$ space velocity).

Thus, it is apparent that there has been provided in accordance with the instant invention, a process that fully satisfies the objects and advantages set forth hereinabove. While the invention has been described with respect to various specific examples and embodiments thereof, it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for the preparation of an iron/lithium-promoted phosphorus-vanadium-oxygen catalyst for the production of maleic anhydride wherein the catalyst has a phosphorus/vanadium atom ratio from about about 0.50 to about 2.00 and an (iron+lithium)-/vanadium atom ratio from about 0.0025 to about 0.0080, with the proviso that the iron/vanadium atom ratio is from about 0.0010 to about 0.0040 and the lithium/vanadium atom ratio is from about 0.0015 to about 0.0040, and with the further proviso that the iron/lithium atom ratio is from about 0.30 to about 1.30, which process comprises:

(a) contacting at least one of each of a substantially tetravalent vanadium-containing compound and a phosphorus-containing compound and a promoter component containing each of iron and lithium in a substantially anhydrous alcohol medium in the presence of anhydrous hydrogen chloride to form a catalyst precursor;

(b) recovering the catalyst precursor;

(c) drying the catalyst precursor at a temperature below that at which crystal phase transformations occur;

(d) roasting the catalyst precursor at a temperature and for a time sufficient to remove residual trace of organic materials; and (e) calcining the roasted catalyst precursor in a series of steps comprising:

(i) heating the roasted catalyst precursor in a dry air atmosphere at a temperature from about 100° C. to about 290° C. for about two hours, (ii) adding water to the dry air atmosphere in an amount sufficient to provide a maximum water concentration of 10% by volume, (iii) increasing the temperature to a value from about 300° C. to about 400° C. at a maximum rate of about 10° C. per hour, (iv) adding a gaseous hydrocarbon convertible to maleic anhydride to the water-containing air stream during step (iii) at a temperature less than the phase transformation temperature in an amount sufficient to provide a hydrocarbon concentration from about 0.5 mole percent to about 1.5 mole percent, and (v) maintaining the temperature from about 300° C. to about 400° C. in step (iii) for a period from about 0.5 hour to about 24 hours, thereby forming the active catalyst.

2. The process of claim 1 wherein the catalyst has a phosphorus/vanadium atom ratio from about 0.95 to about 1.20.

3. The process of claim 1 wherein the catalyst has an iron/vanadium atom ratio from about 0.0015 to about 0.0035 and the lithium/vanadium atom ratio is from about 0.0025 to about 0.0035.

4. The process of claim 1 wherein the phosphorus/vanadium/promoter component atom ratio is about 1.20/1.00/0.0043–0.0063.

5. The process of claim 1 wherein the tetravalent vanadium is formed by the in situ reduction of a pentavalent vanadium-containing compound.

6. The process of claim 5 wherein the pentavalent vanadium-containing compound is a vanadium oxide.

7. The process of claim 6 wherein the vanadium oxide is vanadium pentoxide.

8. The process of claim 1 wherein the substantially anhydrous alcohol medium is isobutyl alcohol.

9. The process of claim 1 wherein the catalyst precursor is recovered by evaporation of the alcohol medium.

10. The process of claim 1 wherein the catalyst precursor is dried at a temperature less than 180° C. for about one hour to about 10 hours.

11. The process of claim 10 wherein the temperature is between 100° C. and about 150° C.

12. The process of claim 1 wherein the catalyst precursor is roasted at a temperature from about 200° C. to about 290° C. for a period of at least two hours.

13. The process of claim 1 wherein the dried catalyst precursor is formed into structures prior to roasting in step (d).

14. The process of claim 1 wherein the hydrocarbon is introduced in step (iv) at a temperature from about 275° C. to about 290° C.

15. The process of claim 1 wherein the temperature maintenance period ranges from about one hour to about six hours.

* * * * *